United States Patent [19]

Kaesemeyer

[11] Patent Number: 5,767,160
[45] Date of Patent: Jun. 16, 1998

[54] METHOD AND FORMULATION OF STIMULATING NITRIC OXIDE SYNTHESIS

[75] Inventor: W. H. Kaesemeyer, Augusta, Ga.

[73] Assignee: Notol, Inc., Augusta, Ga.

[21] Appl. No.: 693,882

[22] Filed: Aug. 5, 1996

Related U.S. Application Data

[63] Continuation-in-part of Ser. No. 321,051, Oct. 5, 1994, Pat. No. 5,543,430.

[51] Int. Cl.$^6$ ............................................. A61K 31/195
[52] U.S. Cl. ........................................................ 514/565
[58] Field of Search ............................................. 514/565

[56] References Cited

U.S. PATENT DOCUMENTS

| | | |
|---|---|---|
| 4,686,211 | 8/1987 | Hara et al. . |
| 5,059,712 | 10/1991 | Griffith . |
| 5,132,407 | 7/1992 | Stuehr et al. . |
| 5,132,453 | 7/1992 | Griffith . |
| 5,158,883 | 10/1992 | Griffith . |
| 5,196,195 | 3/1993 | Griffith . |
| 5,266,594 | 11/1993 | Dawson et al. . |
| 5,273,875 | 12/1993 | Griffith . |
| 5,281,627 | 1/1994 | Griffith . |
| 5,286,739 | 2/1994 | Kilbourn et al. . |

OTHER PUBLICATIONS

Patel, J. M. et al. Nitric Oxide Exposure and Sulfhydryl Modulation Alter L–Arginine Transport in Cultured Pulmonary Artery Endothelial Cells. (Abstract Only) Free Radical Biology & Medicine. vol. 20, No. 5. p. 629. 1996.

Lee, T. J. F. et al. Inhibition of Cerebral Neurogenic Vasolidation by L–Glutamine and Nitric Oxide Synthase Inhibitors and Its Reversal by L–Citruline. The Journal of Pharmacology and Experimental Therapeutics. vol. 276, No. 2. pp. 353–358. 1996.

Horn, M. et al. Preservation of Left Ventricular Mechanical Function and Energy Metabolism in Rats After Myocardial Infarction by the Angiotesin–Converting Enzyme Inhibitor Quinapril. (Abstract Only) Journal of Cardiovascular Pharmacology. vol. 27. p.201. 1996.

Quigley, R. L. et al. Immediate Hemodynamic Effects of Thrombolytic Therapy on the Ischemic Myocardium. Catherization and Cardiovascular Diagnosis. vol. 38. pp. 325–330. 1996.

Abou–Mohamed, G. et al. L–Arginine in the Development and Reversal of Tolerance to Nitroglycerin. (Abstract Only) FASEB J. vol. 10, No. 3. p. A569(no.3280) 1996.

Edner, M. et al. Effect of Enalapril Initiated Early after Acute Mycardial Infarction on Heart Failure Parameters, with Reference to Clinical Class and Echocardiographic Determinants. Clin. Cardiol. vol. 19, pp. 543–548. 1996.

Saaverdra, J. E. et al. Localizing Antithrombolic and Vasodilatory Activity with a Novel, Ultrafast Nitric Oxide Donor. Journal of Medicinal Chemistry. vol. 39, No. 22. pp. 4361–4365. 1996.

Mori, K. et al. Endothelium–Dependent Relaxation of Rat Thoracic Aorta by Amrinone–Induced Nitric Oxide Release. (Abstract Only) The European Society of Cardiology. 1996.

Schwarzacher, S. P. et al. Local Delivery of L–Arginine Increases Vascular Nitric Oxide Production and Improves Endothelium Dependent Vasomotion. (Abstract Only) JACC. No. 779–6. p. 288A Feb. 1996.

Fayyaz, M. et al. Antioxidants Are Vasodilators. JACC. No. 933–88. p. 130A. Feb. 1996.

Daghigh, F. et al. Chemical Modification and Inactivation of Rat Liver Arginase by N–Bromosuccinimide: Reaction with His141. (Abstract Only) Archives of Biochemistry & Biophysics. vol. 327. pp. 107–112. Mar. 1, 1996.

Xia, Y. et al. Nitric Oxide Synthase Generates Superoxide and Nitric Oxide in Arginine–Depleted Cells Leading to Peroxynitrite–Mediated Cellular Injury. Proc. Natl. Acad. Sci. USA. vol. 93. pp. 6770–6774. Jun. 1996.

Rector, T. S. et al. Randomized, Double–Blind, Placebo–controlled Study of Supplemental Oral L–Arginine in Patients With Heart Failure. Circulation. vol. 93, No. 12. pp. 2135–2141. Jun. 15, 1996.

Jeremy, R. W. et al. Effects of Dietary L–Arginine on Atherosclerosis and Endothelium–Dependent Vasolidation in the Hypercholesteralemic Rabbit. Circulation. vol. 94, No. 3. pp. 498–506. Aug. 1, 1996.

Block, E. R. et al. Hypoxia Inhibits L–Arginine Uptake By Pulmonary Artery Endothelial Cells. (Abstract Only) Am. J. Physiol. vol. 269. L574–L580. 1995.

Mayer, J. E. et al. Effects of L–Arginine and L–Nitro–Arginine Methyl Ester on Recovery of Neonatal lamb Hearts After Cold Ischemia. (Abstract Only) J Thoracic Cardiovasc Surg. vol. 109. pp. 81–87. 1995.

Lee, T. J. F. et al. Inhibition of Cerebral Neurogenic Vasodilation by L–Glutamine and Nitric Oxide Synthase Inhibitors and Its Reversal by L–Citrulline. The Journal of Pharmacology and Experimental Therapeutics. vol. 276. No. 2. pp. 353–358. 1996.

Xabregas, A. et al. Nitric Oxide, L–Arginine, Hypertension and Cardiopulmonary Bypass Three Case Reports. Applied Cardiopulmonary Pathophysiology. vol. 5. pp. 231–236. 1995.

(List continued on next page.)

*Primary Examiner*—Paul J. Killos
*Attorney, Agent, or Firm*—Reed Smith Shaw & McClay; Raymond A. Miller

[57] ABSTRACT

A therapeutic in vitro or in vivo mixture comprising L-arginine and an agonist of nitric oxide synthase, namely nitroglycerin is disclosed for the treatment of diseases related to vasoconstriction, wherein the vasoconstriction is relieved by stimulating the constitutive form of nitric oxide synthase (cNOS) to produce native nitric oxide (NO). The native NO having superior beneficial effect when compared to exogenous NO produced by a L-arginine independent pathway in terms of the ability to reduce clinical endpoints and mortality.

20 Claims, 5 Drawing Sheets

OTHER PUBLICATIONS

Castillo, L. et al. Plasma Arginine, Citrulline, and Ornithine Kinetics in Adults, with Observations on Nitric–Oxide Synthesis. (Abstract Only) American Journal of Physiology–Endocrinology and Metabolism. vol. 31, No. 2. pp. E 360–E 367. Feb. 1995.

Hecker, M. et al. Inhibition of Arginase by NG–Hydroxy-–L–Arginine in alveolar macrophages: Implications for the Utilization of L–Arginine for Nitric Oxide Synthesis. FEBS Letters. vol. 359(2–3). pp. 251–254. Feb. 13, 1995.

Wolf, Y. G. et al. Nitroglycerin Decreases Medial Smooth Muscle Cell Proliferation After Arterial Balloon Injury. J Vasc Surg. vol. 21. pp. 499–504. Mar. 1995.

Yu, Y. M. et al. Plasma Arginine and Leucine Kinetics and Urea Production Rates in Burn Patients. (Abstract Only) Metabolism–Clinical and Experimental. vol. 44, No. 5. pp. 659–666. May 1995.

Beaumier, L. et al. Urea Cycle Intermediate Kinetics and Nitrate Excretion at Normal and Therapeutic Intakes of Arginine in Humans. (Abstract Only) American Journal of Physiology–Endocrinology and Metabolism. vol. 32, No. 5. pp. E 884–E 896. Nov. 1995.

Sessa, W. C. the Nitric Oxide Synthase Family of Proteins. J Vasc Res. vol. 31. pp. 131–143. 1994.

Cloaree–Blanchard, L. et al. Rapid Development of Nitrate Tolerance in Healthy Volunteers: Assessment Using Spectral Analysis of Short–Term Blood Pressure and Heart Rate Variability. (Abstract Only) Journal of Cardiovascular Pharmocology. vol. 24. pp. 266–273. 1994.

Celermajer, D. S. et al. Role of Endothelium in the Maintenance of Low Pulmonary Vascular Tone in Normal Children. (Abstract Only) Circulation. vol. 89(5). pp. 2041–2044. 1994.

Boesgaard, S. et al. Nitrate Tolerance in Vivo Is Not Associated With Depletion of Arterial or Venous Thiol Levels. Circulation Research. vol. 74, No., 1. pp. 115–120. Jan. 1994.

Hrabak, A. et al. Comparison of Substrate and Inhibitor Specificity of Arginase and Nitric Oxide (NO) Synthase for Arginine Analogues and Related Compounds in Murine and Rat Macrophages. (Abstract Only) Biochemical & Biophysical Research Communications. vol. 198(1). pp. 206–212. Jan. 14, 1994.

Fujita, H. et al. The Improved Myocardial Perfusion By L–Arginine in Patients with Vasospastic Angina. (Abstract Only) JACC. Abstracts No. 877–22. p. 201A. Feb. 1994.

Faraci, F. M. et al. Nitric Oxide and the Cerebral Circulation. Stroke. vol. 25, No. 3. pp. 692–702. Mar. 1994.

Drexler, H. et al. Effect of L–Arginine on Coronary Endothelial Function in Cardiac Transplant Recipients. Circulation. vol. 89, No. 4. pp. 1615–1623. Apr. 1994.

Fuentes, J. M. et al. Kinetics of Manganese Reconstruction and Thiol Group Exposition in Dialyzed Rat Mammary Gland Arginase. (Abstract Only) International Journal of Biochemistry. vol. 26(15). pp. 653–659. May 1994.

Castillo, L. et al. The Plasma Flux and Oxidation Rate of Ornithine Adaptively Decline with Restricted with Restricted Arginine Intake. (Abstract Only) Proceedings of the National Aadamy of Sciences of the United State of America. vol. 91, No. 14. pp. 6393–6397. Jul. 5, 1994.

Fukuto, D. F. et al. Inhibition of Rat Liver Arginase by an Intermediate in NO Biosynthesis, NG–Hydroxyl–L–Arginine: Implications for the Regulation of Nitric Oxide Biosynthesis by Arginase. (Abstract Only) Biochemical & Biophysical Research Communication. vol. 202(1). pp. 174–180. Jul. 15, 1994.

Reczkowski, R. S. et al. Rat Liver Arginase: Kinetic Mechanism, Alternate Substrates, and Inhibitors. (Abstract Only) Archives of Biochemisty & Biophysics. vol. 312(1). pp. 31–37. Jul. 1994.

Kumagai, K. et al. Nitric Oxide Increases Renal Blood Flow by Interacting With the Sympathetic Nervous System. Hypertension. vol. 24, No. 2. pp. 220–226. Aug. 1994.

Anderson, T. J. et al. Nitric Oxide and Nitrovasodilators: Similarities, Differences and Potential Interactions. JACC. vol. 24, No. 2. pp. 555–566. Aug. 1994.

Boucher, J. L. et al. N Omega–Hydroxyl–L–Arginine, An Intermediate in the L–Arginine to Nitric Oxide Pathway, is a Strong Inhibitor of Liver and Macrophage Arginase. (Abstract Only) Biochemical & Biophysical Research Communications. vol. 203(3). pp. 1614–1621. Sep. 30, 1994.

Lind, D. S. et al. Endotoxin Stimulates Arginine Transport in Pulmonary Artery Endothelial Cells. (Abstract Only) Surgery. vol. 114. pp. 199–205. 1993.

Kawata, H. et al. Nitroglycerin Improves Functional Recovery of Neonatal Lamb Hearts After 2 Hours of Cold Ischemia. (Abstract Only) Circulation. vol. 88[part 2]. pp. 366–371. 1993.

Feelisch, M. Biotransformation to Nitric Oxide of Organic Nitrates in Comparison to Other Notrovasodilators. European Heart Journal. vol. 14 [Supp. 1]. pp. 123–132. 1993.

De Garavilla, L. et al. lack of Cross–Tolerance Between Nitroglycerin and Endothelium–Derived Relaxing Factor–Mediated Vasoactive Agents in Spontaneously Hypertensive Rats. European Journal of Pharmacology. vol. 234. pp. 77–82. 1993.

Castillo, L. et al. Splanchnic Metabolism of Dietary Arginine in Relation to Nitric–Oxide Synthesis on Normal Adult Man. (Abstract Only) Proceedings of the National Academy of Sciences of the United States of America. vol. 80, No. 1. pp. 193–197. Jan. 1, 1993.

Quyyumi, A. A. et al. Effect of L–Arginine, the Substrate for Nitric Oxide, on Endothelium–Dependent Vasodillation of the Coronary Microvasculature. (Abstract Only) JACC. Abstract No. 883–52. vol. 21, No. 2. p. 151A. Feb. 1993.

Dinerman, J. L. et al. Molecular Mechanisms of Nitric Oxide Regulation. Circulation Research. vol. 73, No. 2. pp. 217–222. Aug. 1993.

Kitamura, Y. et al. Nitric Oxide–Mediated Retinal Arteriolar and Arterial Dilatation Induced by Substance P. Investigative Ophthalmology & Visual Science. vol. 34, No. 10. pp. 2859–2865. Sep. 1993.

Mehta, J. L. et al. Free Radicals, Antioxidants, and Coronary Heart Disease. The Journal of Myocardia Ischemia. vol. 5, No. 8. pp. 31–33, 37–41. Sep. 1993.

Robertson, C. A. et al. Effect of Nitric Oxide Synthase Substrate Analog Inhibitors on Rat Liver Arginase. (Abstract Only) Biochemical & Biophysical Research Communications. vol. 197(2). pp. 523–528. Dec. 15, 1993.

Drexler, H. et al. Correction of Endothelial Dysfunction in Coronary Microcirculation of Hypercholesterolaemic Patients by L–Arginine. The Lancet. vol. 338. pp. 1546–1550. Dec. 21–28, 1991.

Marletta, M. A. Nitric Oxide, Nitrovasodilators and L-Arginine-An Unusual Relationship. Western Journal of Medicine. vol. 154, No. 1.pp. 107–109. Jan. 1991.

Nitroglycerine. American Hosp. Formula Drug Information Directory. 1991.

Mayer, B. et al. Brain Nitric Oxide Synthesis is a Biopterin-and Flavin-Containing Multi-Functional Oxido-Reductase. FEBS 10045. vol. 288, No. 1.2. pp. 187–191. Aug. 1991.

Feelisch, M. et al. Biotransformation of Organic Nitrates to Nitric Oxide By Vascular Smooth Muscle and Endothelial Cells. Biochemical and Biophysical Research Communications, vol. 180, No. 1. pp. 286–293. Oct. 15, 1991.

Zembowicz, A. et al. Nitric Oxide and Another P)otent Vasodilator are Formed From Ng-Hydroxy-L-Arginine by Cultured Endothelial Cells. Proc. (Abstract Only) Natl. Acad. Sci. USA. vol. 88. pp. 11172–11176. Dec. 1991.

Schroder, H. et al. Cross Tolerance to L-Arginine Dependent Guanylate Cyclase Activators in Nitrate-Tolerant LLC-PK Kidney Epithelial Cells. Pol. J. Pharmacol. Pharm. vol. 42. pp. 259–263. 1990.

Verdemikov, Y. P. et al. Endothelium-Derived Relaxing Factor is Not Identical to Nitric Oxide. Nitric Oxide From L-Arginine: A bio-Regulatory System. Elsevier Science Publishers. Chap. 39. pp. 373–377. 1990.

Yang, Z. et al. Endothelium-Derived Nitric Oxide in Human Arteries and Veins. Nitric Oxide From L-Arginine: A bio-Regulatory System Elsevier Science Publishers. Chap. 11. pp. 89–93. 1990.

Sakuma, I. et al. L-Arginine is a Precursor of Endothelium-Derived Relaxing Factor in Various Animal Species and Vascular Beds. Nitric Oxide From L-Arginine: A bio-Regulatory System. Elsevier Science Publishers. Chap. 49. pp. 445–449. 1990.

Sneddon, J. M. et al. Transport and Metabolism of L-Arginine by Bovine Aortic endothelial Cells. Nitric Oxide From L-Arginine: A bio-Regulatory System. Elsevier Science Publishers. Chap. 51. p. 457(Intro Only). 1990.

Smith, R.E.A. et al. Role of Nitric Oxide Synthesis in the Regulation of Coronary Vascular Tone in the Isolated Perfused Rabbit Heart. Cardiovascular Research. vol. 26, pp. 508–512. 1992.

Nakanishi, K. et al. Intracoronary L-Arginine Reperfusion Improves Endothelial Function and Reduces Infarct Size. Am. J. Physiol. pp. H1650–H1658. 1992.

Morikawa, E. et al. L-Arginine Decreases Infract Size Caused By Middle Cerebral Arterial Occlusion in SHR. American Journal of Physiology. vol. 263(5 pt. 2). pp. H1632–H1635. 1992.

Mayhan, W. G. et al. Acetylcholine Induces Vasoconstriction in the Microcirculation of Cardiomyopathic Hamsters: Reversal By L-Arginine. Biochemical and Biophysical Research Communications vol. 184, No. 3. pp. 1372–1377. May 15, 1992.

Weyrich, A. S. et al. The Role of L-Arginine in Ameliorating Reperfusion Injury After Myocardial Ischemia in the Cat. Circulation. vol. 86, No. 1. pp. 279–287. Jul. 1992.

Dinerman, J. L. et al. Interactions Between Nitroglycerin and Endothelium in Vascular Smooth Muscle Relaxation. Am. J. Physiol. vol. 26. pp. H698–H701. 1991.

Richard, V. et al. The L-Arginine-Nitric Oxide Pathway in the Canine Femoral Vascular Bed: In Vitro and In Vivo Experiments. Fundam. Clin. Pharmacol. vol. 5. pp. 777–788. 1991.

Schor, K. et al. Generation of Nitric Oxide from Organic Nitrovasodilators During Passage Through the Coronary Vascular Bed and Its Role in Coronary Vasodilation and Nitrate Tolerance. Blood Vessels. vol. 38. pp. 62–66. 1991. Boesgard, S. et al. JPET. vol. 258. pp. 851–855. 1991.

Schinit, V. B. et al. L-Arginine Evokes Both Endothelium--Dependant and Independant Relaxations in L-Arginine-Depleted Aortas of the Rat. (Abstract Only) Circulation Research. vol. 68. pp. 209–216. 1991.

Ignarro, L. J. et al. Pharmacology of Endothelium-derived Nitric Oxide and Nitrovasodilators. Western Journal of Medicine. vol. 154. No. 1. pp. 51–62. Jan. 1991.

Yang, Z. et al. Endothelium-Derived Nitric Oxide in Human Arteries and Veins. Nitric Oxide From L-Arginine: A bio-Regulatory System. Elsevier Science Publishers. Chap. 41. p. 89(Into Only). 1990.

Gold, M.E. et al. L-Arginine-Dependent Vascular Smooth Muscle Relaxation and cGMP Formation. Am. J. Physiol. vol. 259. pp. H1813–H1821. 1990.

Bredt, D.S. et al. Isolation of Nitric Oxide Synthetase, A Calmodulin-Requiring Enzyme. Proc. Natl. Acad. Sci. USA. vol. 87. pp. 682–685. Jan. 1990.

Weidinger, F. F. et al. Persistant Dysfunction of Regenerated Endothelium After Balloon Angioplasty of Rabbit Iliac Artery. Circulation. vol. 81, No. 5. pp. 1667–1679. May 1990.

Nakaki, T. et al. L-Arginine-Induced Hypotension. The Lancet. p. 696. Sep. 15, 1990.

Chester, A.H. et al. Low Basal and Stimulated Release of Nitric Oxide in Atherosclerotic Epicardial Coronary Arteries. The Lancet. vol. 336. pp. 897–900. Oct. 13, 1990.

Bennet, B.M. et al. Relationship Between Biotransformation of Glyceryl Trintrate and Cyclic GMP Accumlation in Various Cultured Cell Lines. The Journal of Pharmacology and Experimental Therapeutics. vol. 250, No.1. pp. 316–323. 1989.

Gold, M.E. et al. Depletion of Arterial L-Arginine Causes Reversible Tolerance to Endothelium-Dependant Relaxation. Biochemical and Biophysical Research Communications. vol. 164, No. 2. pp. 714–721. Oct. 31, 1989.

Bredt, D.S. et al. Nitric Oxide Mediates Glutamate-Linked Enhancement of cGMP Levels in the Cerebellum. Proc. Natl. Acad. Sci. USA. vol. 86. pp. 9030–9033. Nov. 1989.

Albina, J.E. et al. Arginine Metabolism in Wounds. Am. J. Physiol. vol. 254. pp. E459–E467. 1988.

Arginine Hydrochloride. American Hosp. Form. Drug Inf. Dir. pp. 1418–1420. 1988.

Palmer, R. M. J. et al. Vascular Endothelial Cells Synthesize Nitric Oxide From L-Arginine. Nature. vol. 333. pp. 664–666. Jun. 16, 1988.

Flaherty, J. T. Comparison of Intravenous Nitroglycerin and Sodium Nitroprusside in Acute Myocardial Infarction. The American Journal of Medicine. pp. 53–60, Jun. 27, 1983.

Corrie, G. A. Activated Macrophages Kill Tumur Cells By Releasing Arginase. Nature. vol. 273. pp. 758–759. Jun. 29, 1978.

Flaherty, J. T. et al. Intravenous Nitroglycerin in Acute Myocardial Infarction. Circulation. vol. 51. pp. 132–139. Jan. 1975.

Parker, M. L. et al. The Arginine Provocative Test: An Aid in the Diagnosis of Hyposematotrepism. J. Clin. Endo. vol. 27. pp. 1129–1136. Aug. 1967.

Knopf, et al. Plasma Growth Hormone Response to Intravenous Administration of Amino Acids.Preliminary Communication . vol. 25. pp. 1140–1144. Aug. 1965.

Persson, M.G. et al. Nitric Oxide—More Than a Vasodilator. (Abstract Only) Lakartidningen. vol. 90, No. 14. pp. 1365–1371. Apr. 7, 1993.

Chen, R.Y. et al. Role of L–Arginine–Derived Nitric Oxide in Cholinergic Dilation of Gastric Arterioles. (Abstract Only) Am J. Physiol. vol. 265, No. 6, pt. 2. p. H2110–6. Dec. 1993.

Parent R. et al. Contribution of Nitric Oxide to Dilation of Resistance Coronary Vessels in Conscious Dogs. (Abstract Only) Am. J. Physiol. vol. 262, No. 1, pt. 2. p. H10–6. Jan. 1992.

Smith, R.E. et al. Role of Nitric Oxide Synthesis in the Regulation of Coronary Vascular Tone in the Isolated Perfused Rabbit Heart. (Abstract Only) Cardiovascular Research. vol. 26, No. 5. pp. 508–512. May 1992.

Mayhan, W.G. et al. Acetylcholine Induces Vasoconstriction in the Microcirculation of Cardiomyopathic Hamsters: Reversal by L–Arginine. (Abstract Only) Biochemical and Biophysical Research Communications. vol. 184, No. 3. pp. 1372–1377. May 15, 1992.

Schroder, H. et al. Cross–Tolerance to L–Arginine–Dependant Guanylate Cyclase Activators in Nitrate–Tolerant LLc–PK1 Kidney Epithelial Cells. (Abstract Only) Polish Journal of Pharmacology and Pharmacy. vol. 42, No. 3. pp. 259–263. May–Jun., 1990.

Cooke, J.P. et al. Antiatherogenic Effects of L–Arginine in the Hypercholesterolemic Rabbit. J. Clin. Invest. vol. 90, No. 3. pp. 1168–1172. Sep. 1990.

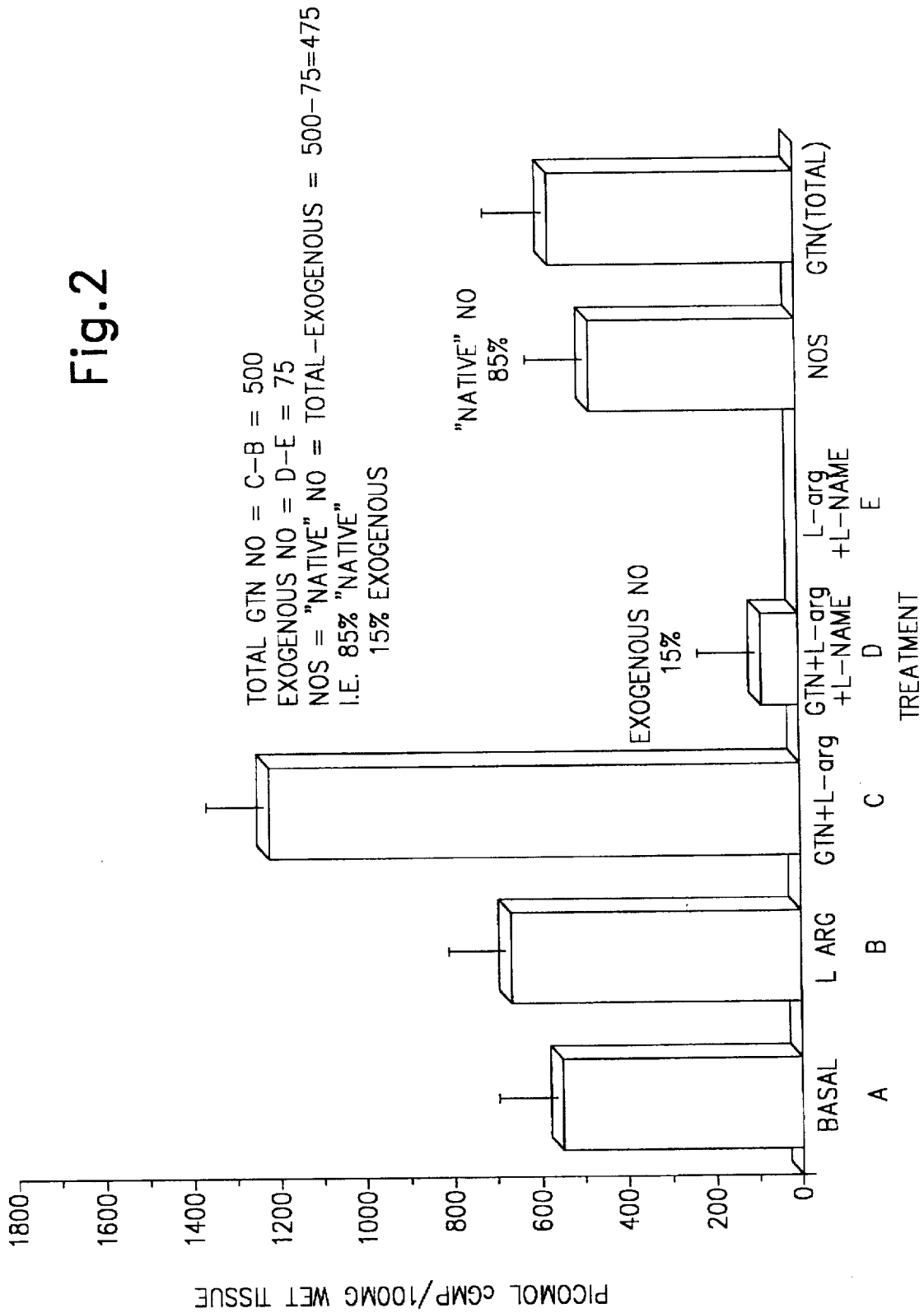

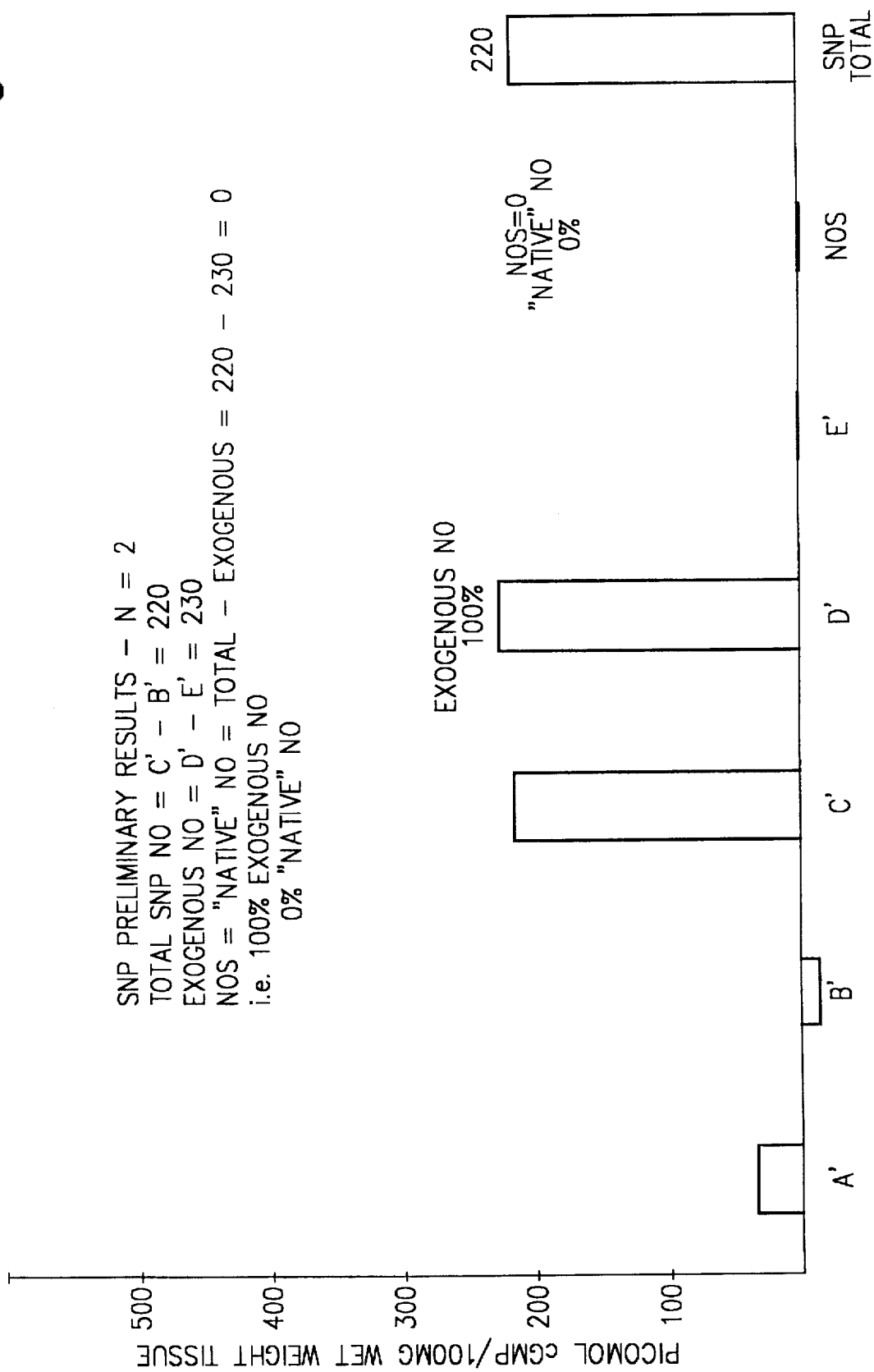

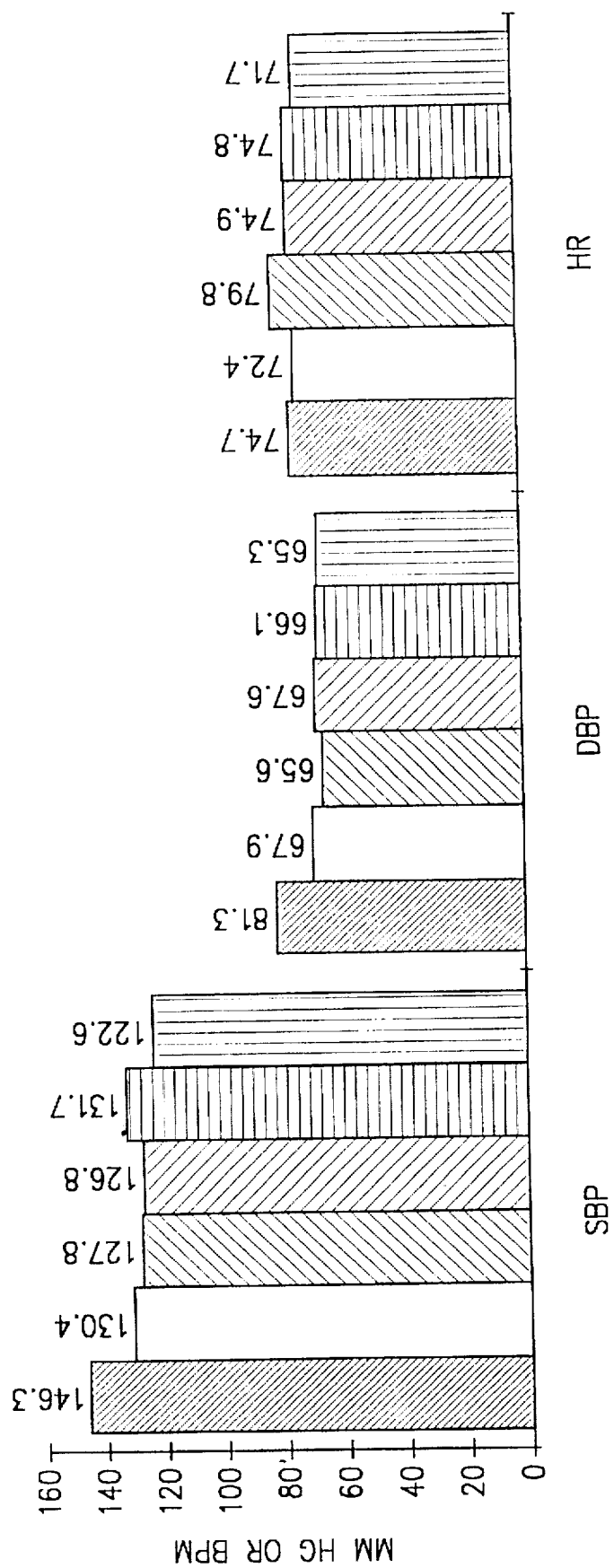

METHOD AND FORMULATION OF STIMULATING NITRIC OXIDE SYNTHESIS

This application is a Continuation-in-Part of Ser. No. 08/321,051 filed Oct. 5, 1994, now U.S. Pat. No. 5,543,430.

BACKGROUND OF THE INVENTION

This invention relates generally to a method of treating hypertensive cardiocerebropulmonorenovascular disease as well as non-hypertensive cardiocerebropulmonorenovascular disease, and a unique formulation used in the treatment of these diseases and their symptoms, wherein an arginine or its biological equivalent and a stimulator of Nitric Oxide Synthase (NOS), particularly nitroglycerin, either in a premix or sequentially administered are utilized.

DESCRIPTION OF RELATED ART

For several decades nitroglycerin has been administered to humans as a vasodilating agent in the treatment of cardiovascular disease. Nitroglycerin or glycerol trinitrate is an organic nitrate ester which when administered to a subject is converted biologically to nitric oxide (NO) which is a pharmacologically active metabolite. NO, for example, activates soluble guanylate cyclase in vascular smooth muscle cells which in turn increase cyclic guanosine monophosphate (cGMP) resulting in vasorelaxation. (Waldman et al., 1987, *Cyclic GMP synthesis and function*, Pharmacol. Rev. 39, 163.) and ultimately leads to vasodilation and a reduction in blood pressure. However, the effectiveness of nitroglycerin is greatly diminished because the recipient of therapeutic administration of nitroglycerin rapidly develops a tolerance to the beneficial effects of nitroglycerin. Therefore, onset of nitroglycerin tolerance significantly limits the therapeutic value of nitroglycerin because increased dosages have little or no effect on vasorelaxation or vasodilation. (Bogaert, M., 1991, *Clinical relevance of tolerance to nitrovasodilators*, J. Cardiovas. Pharmacol. 17 (Suppl. 3), S313; and Unger, P., et al., 1991, *Tolerance to intravenous nitrates*, J. Cardiovasc. Pharmacol. 17 (Suppl. 3), S300.) The precise mechanism of nitroglycerin tolerance is unknown. Theories explaining the tolerance include: the sulfhydryl pools necessary for the direct biotransformation of nitroglycerin into active nitric oxide are depleted by excess nitroglycerin substrate. (Boesgaard, S., et al., 1991, *Nitrate tolerance: effect of thiol supplementation during prolonged nitroglycerin infusion in an in vivo rat model*, J. Pharmacol. Exp. Ther. 258, 851); the activation of vascular guanylate cyclase is diminished by nitroglycerin (Henry P. J., et al., 1989, *S-Nitrosothiols as vasodilators: Implications regarding tolerance to nitric-oxide-containing vasodilators*, Br. J. Pharmacol. 98, 757); or that the rate of cGMP degradation may be increased during tolerance to nitroglycerin (Axelsson, K. L., et al., 1987, *Nitrate tolerance from a biochemical point of view*, Drugs 33, 63).

Recently, nitric oxide has also been shown to be formed enzymatically as a normal metabolite from arginine in vascular endothelium to provide an important component to the formation of endothelium-derived relaxing factor (EDRF). Macrophages and neurons have also been shown to produce nitric oxide in the body as a component of their cell killing and/or cytostatic function.

More recently it has been established that a family of enzymes called NOS form nitric oxide from L-arginine, and the nitric oxide produced is responsible for the endothelium dependent relaxation and activation of soluble guanylate cyclase, neurotransmission in the central and peripheral nervous systems, and activated macrophage cytotoxicity (Sessa, William C., 1994, *The Nitric Oxide Synthase Family of Proteins*, Review, pp. 131-143,).

Nitric Oxide Synthase, occurs in many distinct isoforms which include a constitutive form (cNOS) and an inducible form (iNOS). The constitutive form is present in normal endothelial cells, neurons and some other tissues. Formation of nitric oxide by the constitutive form in endothelial cells is thought to play an important role in normal blood pressure regulation. The inducible form of nitric oxide synthase has been found to be present in activated macrophages and is induced in vascular smooth muscle cells, for example, by various cytokines and/or microbial products. It is thought that in sepsis or cytokine-induced shock, overproduction of nitric oxide by the inducible form of nitric oxide synthase plays an important role in the observed life-threatening hypotension.

As discussed above, the conversion of L-arginine into nitric oxide is enzymatically catalyzed by NOS and the resulting by product is L-citrulline. There is a pathway for the re-conversion of L-citrulline to l-arginine, and accordingly L-citrulline can be considered a biological equivalent of L-arginine. Although it was initially described in endothelium, as discussed above, NOS activity has now been described in many cell types. Brain, endothelium, and macrophage isoforms appear to be products or different genes that have approximately 50% amino acid identity. NOS in brain and in endothelium have very similar properties, the major differences being that brain NOS is cytosolic and the endothelial enzyme is mainly a membrane-associated protein.

Functionally, the constitutive form of Nitric Oxide Synthase (cNOS), which is the predominant synthase present in brain and endothelium, may be active under basal conditions and can be further stimulated by increases in intracellular calcium that occur in response to receptor-mediated agonists or calcium ionophores. cNOS appears to be the "physiological" form of the enzyme and plays a role in a diverse group of biologic processes. In vitro studies suggest that the activity of nitric oxide synthase can be regulated in a negative feedback manner by nitric oxide itself; however, more recent data suggests that the nitric oxide effect on EDRF production is through inhibition of L-arginine uptake into endothelial cells. As a result of oxidation of sulfhydryl groups in the sodium independent and sodium dependent L-arginine pathway. In the cardiocerebropulmonorenovascular circulation, the primary target for constitutively produced nitric oxide is soluble guanylate cyclase located in vascular smooth muscle, the myocardium (myocytes) and coronary vascular smooth muscle.

In the presence of normal substrate, nitric oxide is made preferentially by nitric oxide synthase. However, in the absence of L-arginine, brain nitric oxide synthase is thought to generate the free radicals superoxide and hydrogen peroxide. This property of nitric oxide synthase has potential major implications for neurotoxicity and pathophysiological conditions such as ischemia.

In contrast, to the constitutive form of the enzyme, the inducible, calcium-independent form was initially only described in macrophages. It is now known that induction of nitric oxide synthase can occur in response to appropriate stimuli in many other cell types. This includes both cells that normally do not express a constitutive form of nitric oxide synthase, such as vascular smooth muscle cells, as well as cells such as those of the myocardium (Levine B. et al., 1990, *Elevated circulating levels of tumor necrosis factor in*

*severe chronic heart failure.* N Engl J med. 323:236–241.) that express considerable levels of the constitutive isoform.

iNOS exhibits negligible activity under basal conditions, but in response to factors such as lipopolysaccharide and certain cytokines. expression occurs over a period of hours. The induced form of the enzyme produces much greater amounts of NO than the constitutive form. and induced NOS appears to be the "pathophysiological" form of the enzyme because high concentrations of NO produced by iNOS can be toxic to cells. Induction of iNOS can be inhibited by glucocorticoids and some cytokines. Relatively little is known about postranscriptional regulation of iNOS. Cytotoxic effects of NO are probably largely independent of guanylate cyclase and cyclic GMP formation.

Most of the research in the area has focused on inhibitors of iNOS stimulation using various derivatives of L-arginine. However little research has been done on the stimulation of cNOS and its effect on nitroglycerin tolerance. Nitroglycerin tolerance has continued to frustrate the health care community because there is to date no effective way to stimulate physiological NO production above the tolerance or resistance floor of nitroglycerin so as to maintain the beneficial effect of the administration of nitroglycerin for prolonged periods.

An effective method of treating hypertensive cardiocerebropulmonorenovascular diseases and symptoms as well as non-hypertensive cardiocerebrorenovascular diseases and symptoms so as to overcome the resistance-tolerance floor of nitroglycerin is needed in the art.

SUMMARY OF THE INVENTION

The term "subject" is used herein to mean any mammal, including humans, where nitric oxide formation from arginine occurs. The methods herein for use on subjects contemplate prophylactic use as well as curative use in therapy of an existing condition. The term "native NO" as used herein refers to the nitric oxide that is produced through the biotransformation of L-arginine or the L-arginine dependent pathway. The term endpoints as used herein refers to clinical events encountered in the course of treating cardiovascular disease. up to and including death (mortality)

It is an object of this invention to treat pharmacological tolerance to nitroglycerin.

It is another object of this invention to provide a method of preventing. treating. arresting. or ameliorating disease conditions which are benefitted by the biotransformation of L-arginine into endogenous nitric oxide or "native" nitric oxide.

It is another object of this invention to provide the sequential administration of L-arginine and its biological equivalence with an arterial dilator or NO agonist.

It is another object of this invention is to provide a formulation that has a combined arterial and veno dilatory effect.

It is another object of this invention to ameliorate or avoid tachycardia and prevent or treat ischemia.

It is another object of this invention to premix L-arginine and nitroglycerin to achieve a synergistic effect to treat nitroglycerin tolerance by increasing or maximizing the ability of nitroglycerin to produce "native" nitric oxide, and reduce clinical endpoints to include mortality.

It is another object of this invention to prevent reperfusion injury in subjects who have had abrupt restoration of blood flow.

It is another object of this invention to use the combination or mixture formed to reduce the dosage requirements of L-arginine and the corresponding deleterious consequences of volume overload.

It is another object of this invention to provide a stable mixture of nitroglycerin and L-arginine which stabilizes the explosive and decomposition properties of nitroglycerin in a mixture.

It is a further object of this invention to provide a mixture of nitroglycerin and L-arginine for the treatment of hypertension. hypertensive heart disease; coronary heart disease. including angina. myocardial infarction. and sudden death; and a wide range of cardiovascular disease (heart failure, stroke, and peripheral vascular diseases). and renovascular ischemia/hypertension.

It is another object of this invention to administer an acitail cistine or other similar self-hyrdial containing compounds to the mixture which is administered sequentially or as a premix to reduce sulfhydryl groups which are oxidized in a cell.

These and other objects of this invention are provided by one or more of the embodiments provided below.

In one embodiment of the invention, therapeutically effective amounts of L-arginine and a cNOS agonist are mixed together prior to administration to a subject. Mixing in the general sense can refer to in vivo mixing due to sequential or concomitant administration of two or more compounds.

It is another object of this invention to administer L-arginine alone to saturate cell processes with L-arginine thereby eliminating or improving tolerance to nitroglycerin or other vasodilator compounds.

In another embodiment of the invention, therapeutically effective amounts of L-arginine and nitroglycerin are combined at a physiologically acceptable pH prior to administration.

It is another object of this invention to utilize biologically equivalence of L-arginine or precursors to L-arginine in place of L-arginine in the premixture or sequential administration. Such precursors include L-citrulline which is a precursor to L-arginine via the L-citrulline-L-arginine recycle pathway.

In another embodiment a method for treating hypertension in a subject by vasodilation or vasorelaxation comprises: selecting a hypertensive subject; administering to said subject an anti-hypertensive formulation comprising a mixture of a venous dilator; and an arterial dilator; obtaining periodic blood pressure measurements of the subject; and; continuing administration of the formulation until a desirable blood pressure or therapeutic effect is detected in the subject. A desirable blood pressure in a hypertensive subject should ultimately be within the following ranges: systolic preferably in the range of 95–180 mmHg. more preferably in the range of 105–165 mmHg. and even more preferably in the range of 120 to 140 mmHg; and diastolic preferably in the range of 55–115 mmHg. more preferably in the range of 65–100 mmHg. and even more preferably in the range of 70 to 90 mmHg. and most preferably 75–85 mmHg. Under no circumstances should the systolic be permitted to go below 95 mmHg.

Another embodiment is a method for preventing or treating cardiovascular disease in a non-hypertensive subject by vasodilation or vasorelaxation comprising: selecting a subject; administering to said subject a formulation comprising a mixture of a venous dilator and an arterial dilator wherein the venous dilator is a combined non-endothelium and endothelium dependent source of nitric oxide (i.e.

nitroglycerin) and said arterial dilator is an endothelium dependent source of nitric oxide (L-arginine); obtaining periodic measurements of vasorelaxation on the subject and; continuing administration of the formulation until a desirable state of vasorelaxation or desirable therapeutic effect is detected on the subject. A desirable state of vasorelaxation is for example a lowering of the systolic by about 20 mmHg and a lowering of the diastolic by about 10 mmHg. Under no circumstances should the systolic be lowered less than 95 mmHg.

Yet another embodiment is a method for treating hypertension in a subject by vasodilation comprising: selecting a hypertensive subject; administering to said subject an anti-hypertensive formulation comprising a mixture of L-arginine and nitroglycerin; obtaining periodic blood pressure measurements on the subject; and; continuing administration of the anti-hypertensive formulation until a desirable blood pressure is detected in the subject.

Another embodiment is the treatment of nitrate tolerance in a subject which comprises administering a biological equivalent of L-arginine to said subject to saturate the cells and sequentially or concurrently administering a nitrate (nitroglycerin) to said subject; obtaining periodic indicators of vasorelaxations for the subject; and continuing administration of said L-arginine until tolerance is treated.

Yet another embodiment is a method for stimulating cNOS in a subject which comprises: selecting a subject; administering to said subject a formulation comprising a mixture of L-arginine and nitroglycerin, so as to maximize "native" NO production in order to treat tolerance and reduce endpoints to include mortality.

BRIEF DESCRIPTION OF THE DRAWINGS

FIG. 2 is a bar graph illustrating the cNOS stimulating effect of combined administration of L-arginine and nitroglycerin on rat aorta.

FIG. 3 is a bar graph illustrating the absence of cNOS stimulating effect of combined administration of L-arginine and SNP on rat aorta.

FIG. 4 is a human dose study which demonstrates the absence of tachycardia during administration of the herein described formulation.

DETAILED DESCRIPTION OF THE PREFERRED EMBODIMENTS

Figure 1A:
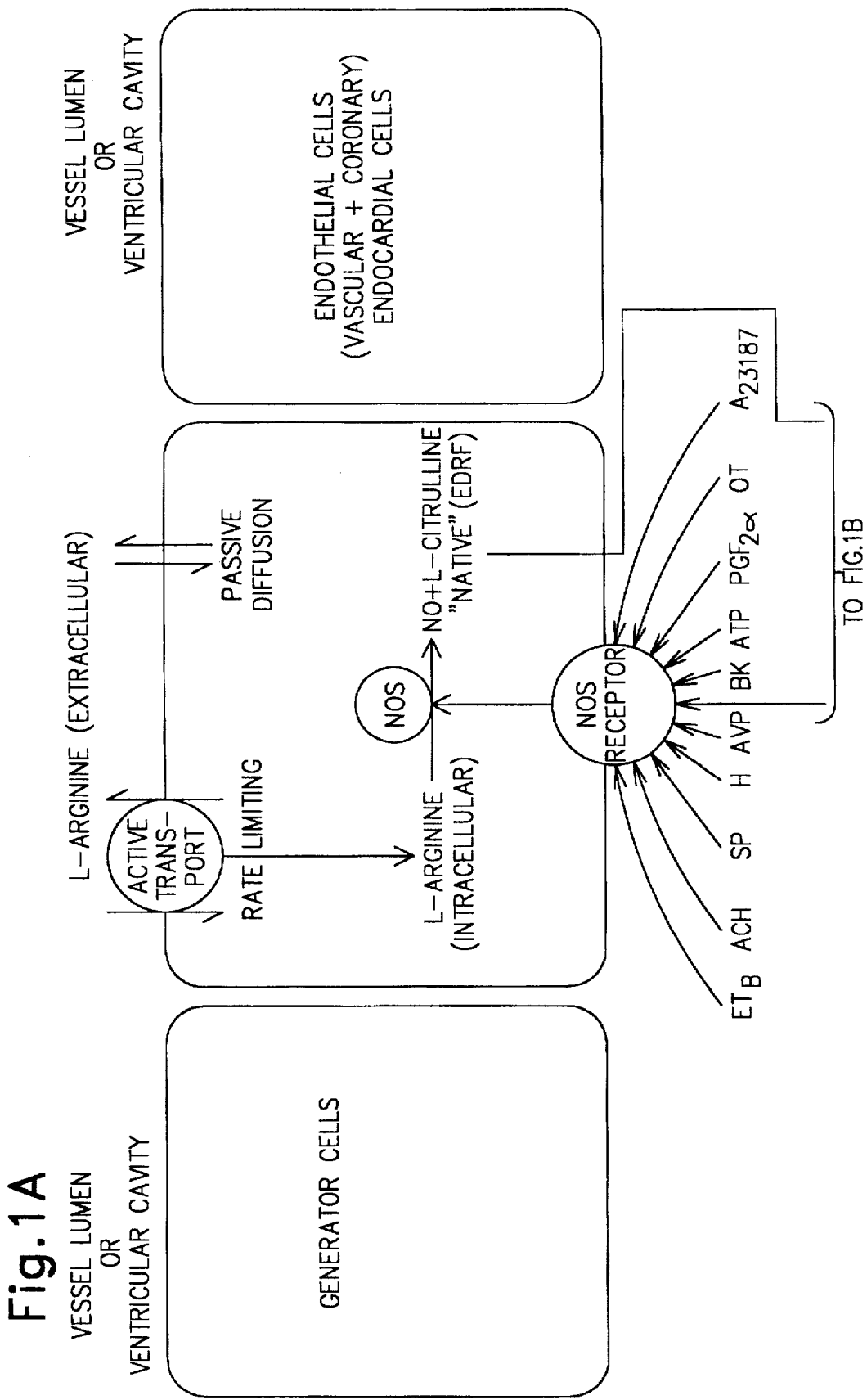
FIG. 1A is the top portion of a schematic representation of the proposed L-arginine dependent and independent pathways.

It has been discovered that combining L-arginine or biologically equivalents thereto with nitroglycerin prior to administration overcomes the resistance or tolerance level normally established when administering nitroglycerin alone. It is believed that NOS may be stimulated by nitroglycerin and that premixing with L-arginine has a synergistic beneficial effect that may be due to a complex or coordinate formation between nitroglycerin and L-arginine. Excess L-arginine provides additional substrate for the stimulated nitric oxide synthase which catalyzes the biotransformation of L-arginine into nitric oxide. As used herein a "biological equivalent" is an agent or composition, or combination thereof, which has a similar or identical biological function or effect as the agent or composition to which it is being deemed equivalent. For example, a biological equivalent of arginine is a chemical compound or combination of chemical compounds which has the same or similar biological function or effect as arginine.

Such stimulation of NOS in the presence of excess L-arginine may be used to prevent, treat, arrest, or ameliorate any disease or condition which may be positively affected by NO production. Such conditions include hypertensive cardiocerebropulmonorenovascular diseases and symptoms as well as non-hypertensive cardiocerebropulmonorenovascular diseases. The mixture is particularly useful for subjects in need of native NO production. Application of such a mixture is beneficial for: (1) Chronic stable angina; (2) Unstable angina; (3) Acute myocardial infarction; (4) Hibernating myocardium; (5) Stunned myocardium; (6) Limitation of ventricular remodeling in post myocardial infarction and subsequent risk of congestive heart failure; (7) Prophylaxis of recurrent myocardial infarction; (8) Prevention of sudden death following myocardial infarction; (9) Vasospastic angina; (10) Congestive heart failure-systolic-seen in association with 1–6 above; (11) Congestive heart failure-diastolic-seen in association with 1–10 above and 12–15 below; (12) Microvascular angina seen in association with 1–11 above and 15 and 16 below; (13) Silent ischemia seen in association with 1–12 above and 15 and 16 below; (14) Reduction of ventricular ectopic activity seen in association with 1–13 above and 15 below; (15) Any or all of the above 1–14 states of ischemic myocardium associated with hypertensive heart disease and impaired coronary vasodilator reserve; (16) control of blood pressure in the treatment of hypertensive crisis, perioperative hypertension, preaclampsia or aclampsia uncomplicated essential hypertension and secondary hypertension; (17) Regression of left ventricular hypertrophy seen in association with 15 and 16 above; (18) Prevention and or regression of epicardial coronary atherosclerosis seen in 1–17 above; (19) Prevention of restenosis post angioplasty; (20) Prevention and/or amelioration of free radical mediated reperfusion injury in association with 1–19 above; (21) Use of the combination in the prevention of myocardial injury during cardioplegic arrest during coronary bypass or other open heart surgery i.e. use of the combination as a cardioplegic solution; (22) Post transplant cardiomyopathy; (23) Renovascular ischemia; (24) Cerebrovascular ischemia (Transient Ischemic Attack (TIA) and stroke); 25 pulmonary hypertension.

Figure 1B:
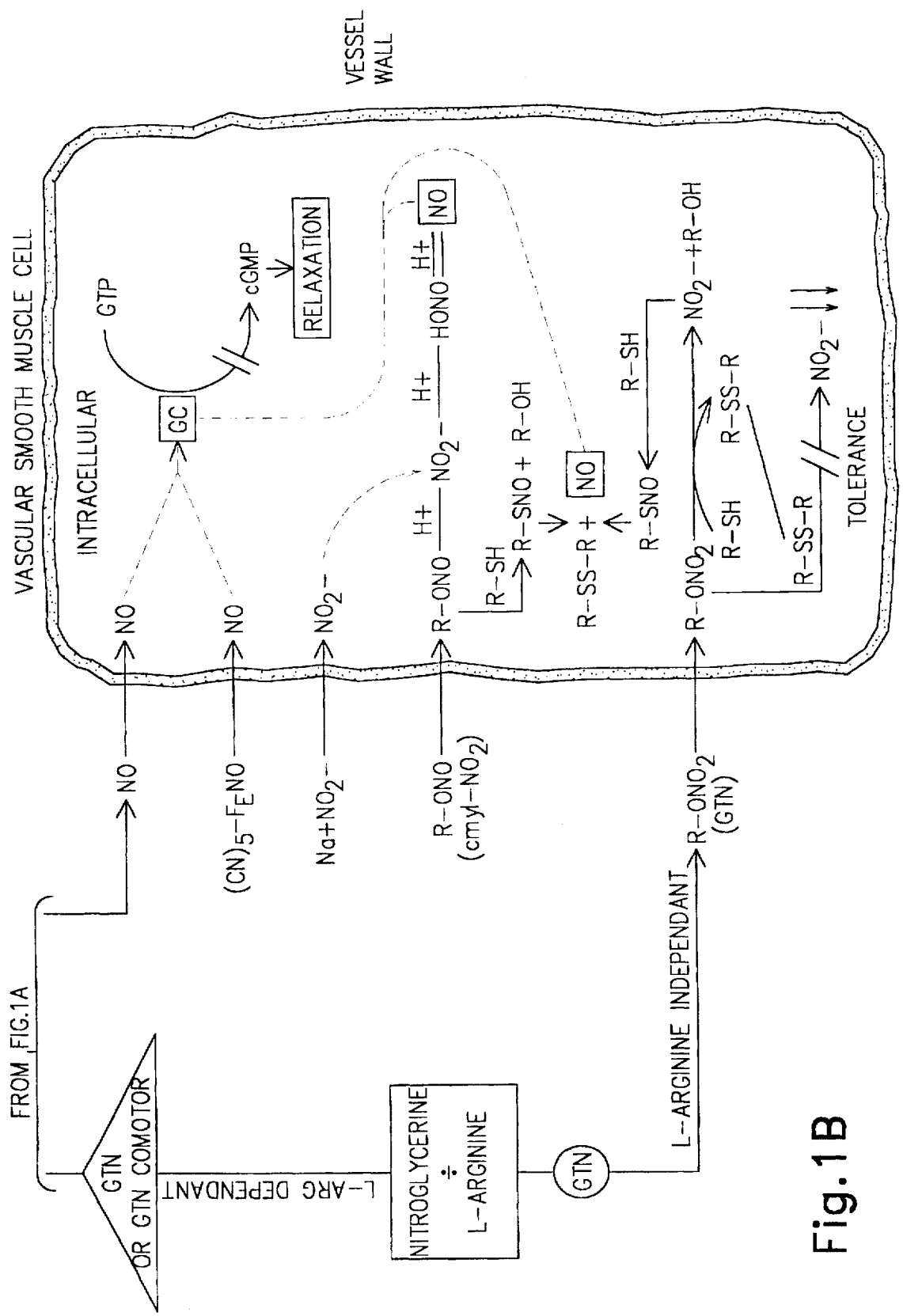
FIG. 1B is the bottom portion flowing from FIG. 1A of a schematic representation of the proposed L-arginine dependent and independent pathways.

FIG. 1A and FIG. 1B illustrate a schematic representation of the proposed mechanism of action elicited by nitrovasodilators on both a generator cell and a target cell and their interrelationship. It appears that nitroglycerin or glycerol trinitrate's (GTN) mechanism of action is both L-arginine dependent and L-arginine independent and this implication has far reaching effects regarding the development and treatment of nitroglycerin tolerance and reducing clinical endpoints and mortality. A type of generator cell is an endothelial cell, but may also be an endocardial cell or a coronary neuronal cell; and a corresponding type of target cell is a vascular smooth muscle cell, but may also be a myocardial cell (myocyte). Vascular smooth muscle cells are located mainly in the veins, arteries, and coronary arteries. The following discussion will focus on smooth muscle and myocyte relaxation stimulated by nitrovasodilators wherein the nitric oxide synthase is cNOS, the constitutive form of nitric oxide synthase, the generator cells are endothelial cells and the target cells are vascular smooth muscle cells. This illustration is not intended to imply any cellular relationship between the various sites of action, but rather meant to illustrate their functional relationship.

As shown in FIGS. 1A and 1B the production of NO may result from a variety of sources and mechanisms which are discussed in detail in Ignarro. (Louis J. PhD., 1991, *Pharmacology of Endothelium-Derived Nitric Oxide and Nitrovasodilators*, The Western Journal of Medicine, pp.51–62.) which is incorporated herein in its entirety by reference. In the L-arginine independent or non-endothelium dependent pathway the activation of Guanylate Cyclase (GC) by Nitric Oxide (NO) depends on the type of nitrovasodilator used. Inorganic Nitrite ($NO_2^-$) is charged and only limited amounts can permeate the cell, but intracellular nitrite can be converted to NO. Lipophilic organic nitrate esters (R—OH) are converted into NO by acidic thiol (R—SH) facilitated reactions. S-Nitrosothiols (R—SNO) are labile intermediates that decompose spontaneously and produce NO. It is thought that one of the mechanisms by which thiols potentiate the action of nitroglycerin and reverse to some degree tolerance to nitroglycerin is through the direct reaction between the thiol (R—SH) and nitroglycerin (GTN) to form the labile intermediate S-Nitrosothiol (R—SNO), which decompose as described above (R—SH+ GTN –>R—SNO is not shown). A nonenzymatic formation of exogenous NO is thought to occur with thiol sources such as cysteine, dithiothreitol, N-acetylcysteine, mercaptosuccinic acid, thiosalicylic acid, and methylthiosalicylic acid. Nitrates such as isosorbide dinitrate, and isosorbide 5' mononitrate also can be used to produce NO since they are simply commercially available intermediates to the known L-arginine independent pathway. Nitroprusside (($CN)_5$-FeNO) forms NO upon breakdown and is not thiol dependent. GTP is guanosine triphosphate; HONO is nitrous acid; Meth. Blue is Methylene Blue; R—ONO is organic nitrite esters; and R—SS—R represents a disulfide. In the L-arginine independent pathway the glycerol trinitrate (GTN) reaction is represented by R—$ONO_2$ and are thought to need a certain pool of thiols, such as a sulfhydryl containing enzyme, to generate NO and it was formerly thought that intracellular thiol deficiency results in tolerance to the pharmacological actions of nitroglycerin. This however does not account for the tolerance because exogenous dose dependent thiols do not result in reversal of nitroglycerin tolerance (Fung H. L., 1988, *Journal of Pharmacology and experimental Therapeutics*. 245:2,524–30.) but may exert beneficial effect as independent donors of NO, versus facilitate spontaneous release of nitric oxide. (Munzel T., M.D., et al., 1994, *What Causes Nitroglycerin Tolerance?* Clinical Cardiology. 20 No. 9:40–47.)

However, it is hypothesized that the tolerance to nitroglycerin may involve a secondary pathway, or indeed, this "secondary pathway" may be the primary pathway. This "secondary pathway" is the L-arginine dependent pathway or endothelium dependent pathway shown in FIGS. 1A and 1B. As seen in FIG. 1A, the generator cell is known to have several receptor mediated agonists such as Endothelium B receptor ($ET_B$); acetylcholine (Ach); substance P (SP), Histamine (H); arginine vasopressin (AVP); bradykinin (BK); Adenosine Triphosphate (ATP); Prostaglandin $F_{2\alpha}$ ($F_{2\alpha}$); Oxytocin, (OT); and the calcium ionophore (A23187) which stimulate the production of NOS. However, until now it has not been speculated that nitroglycerin may serve the dual role of agonist for NOS, and pro-drug for the sulfhydryl mediated L-arginine independent pathway.

Previously it was thought that nitroglycerin had no effect on the biotransformation of L-arginine into "native" nitric oxide, but it is now believed that nitroglycerin or a nitroglycerin complex or coordinate with L-arginine has a stimulating effect on cNOS. The mechanism is not well understood but it appears the administration of nitroglycerin and L-arginine either as a premixture or sequentially may have a heretofore unexpected synergistic effect on cNOS stimulation which may be a result of cNOS having a unique receptor site for the nitroglycerin being in a state of disassociation equilibrium with L-arginine. Administering the two in combination or immediately after one another also provides adequate substrate and avoids cNOS processing of L-arginine since the L-arginine will be added in excess. The purpose of the administration is to provide adequate amounts of L-arginine within the generator cell at all times though that nos will not use molecular $O_2$ as an alternative substrate thereby resulting in production of $O_2^-$ and $H_2O_2$.

Combining L-arginine and nitroglycerin may also result in a combined arterial and venous dilatory effect. Used alone nitroglycerin is principally a venodilator at low doses although it can become a veno-arterial dilator at high doses and causes rapid increase in heart beat due to its venous pooling, while L-arginine on the other hand when used alone is principally an arterial dilator. Therefore, combining the two results in balanced arterial and venodilatory effect which counter balances the tendencies of one or the other to produce tachycardia which is adverse to ischemia in an evolving myocardial infarction. This is suggested by preliminary data in dog studies and is most notable in the data shown in Table I. The data in Table I was generated by administering L-Arginine at 5 cc per minute wherein the L-arginine was at 10% w/v (g/ml) and the nitroglycerin was administered at 3.38 μg/kg/minute by Intravenous (IV) administration over a five minute period. The dog was a beagle that weighed 13.6 kg. When administered in combination, the relative concentrations and dosages remained the same. BP is Blood Pressure (systolic/diastolic in mmHg); MAP is Mean Arterial Pressure (mmHg); CO is Cardiac Output (liters/min.); TPVR is Total Peripheral Vascular Resistance (dynes*sec./$cm^3$); ΔTPVR is the change in Total Peripheral Vascular Resistance (%); and HR is Heart Rate (bpm).

TABLE I

Canine Study

| Agent | BP | MAP | CO | (TPVR) | HR | ΔTPVR |
|---|---|---|---|---|---|---|
| Before L-Arginine | 130/75 | 93.3 | 1.44 | (64.8) | 105 | |
| After | 105/55 | 71.7 | 1.62 | (44.3) | 102 | 31.6% |
| Before Nitroglycerin | 105/60 | 75.0 | 1.63 | (46.0) | 104 | |
| After | 70/40 | 50.0 | 1.44 | (34.7) | 105 | 24.5% |
| Before Nitroglycerin + L-Arginine | 105/60 | 75.0 | 1.56 | (48.1) | 102 | |
| After | 70/40 | 50.0 | 1.60 | (31.3) | 98 | 16.8% |

It can be seen from looking at The effect on CO or Cardiac Output that after administration of the L-arginine alone an increase in cardiac output is due to the effect of L-arginine as principally an arterial dilator; and the decrease in cardiac output seen with nitroglycerin alone is principally due to a venous dilatory effect; while the combination produces a substantially balanced arterial and venous dilatory effect (a change in cardiac output of only 0.04 (1.60–1.56)). Hence, the absence of a tendency towards tachycardia (i.e. no evidence of baroreceptor reflex activation).

Another mechanism of benefit from the combination relates to the fact that used alone nitroglycerin is of only minimal benefit in limiting reperfusion injury with patients who have had recent heart attacks and abrupt restoration of blood flow. The same thing is seen in patients who are undergoing re-establishment of blood flow after coronary bypass operations coming off the bypass pump. This form of reperfusion injury is thought to be mediated by free radical generation upon reperfusion and preliminary data especially in cats shows that L-arginine administered alone limits free radical production. (Weyrich, A. S., PhD., et al., 1992, *The Role of L-Arginine in Ameliorating Reperfusion Injury After Myocardial Ischemia in the Cat*. Circulation. 86:279–288.) Therefore, the combination would be likely to limit reperfusion injury relative to nitroglycerin used alone.

Another benefit of the use of the combination relative to each used alone relates to the fact that the volunteer studies thus far with l-arginine alone reveal it to be a weak vasodilator in terms of dosage requirements. (600 cc/hr as reported by Nakaki T., et al., 1990, *L-arginine Induced Hypertension*. The Lancet, p. 696). Patients who have unstable coronary syndromes and myocardial infarction with or without the complication of congestive heart failure are prone to volume overload with administration of IV fluids. Therefore by combining nitroglycerin with L-arginine one could limit remarkably the total L-arginine dosage requirement and thereby the risk for developing congestive heart failure. This might also be of importance in patients who have compromised renal function and are prone to acidosis and renal failure with large volumes of L-arginine.

The principle combination to be employed will be a mixture that involves therapuetic concentrations of L-arginine and nitroglycerin in water. Any pharmaceutical grade L-arginine will be sufficient and should be diluted preferably to 2.5–60% w/v (g/ml), more preferably to 5–45% w/v (g/ml), even more preferably between 7.5–30% w/v (g/ml), even more preferably to 10–15% w/v (g/ml), and most preferably 10% w/v (g/ml) L-arginine. The typical doses anticipated will be 30 grams of L-arginine in sterile water (Total Volume 300 cc). The L-arginine is anticipated eventually to be approximately 10:1 to about 25:1 of the hydrochloride salt: L-arginine as a base, and even more preferably 15:1 to about 20:1 hydrochloride salt to base, and most preferably 15:1 hydrochloride salt to base. In this example 28 to 29 grams will be the hydrochloride salt and 1 to 2 grams of L-arginine will be base. It is anticipated that the nitroglycerin to be combined with L-arginine will have a concentration dependent on the mass of the subject in kg and dosage time preferably in the range of 0.1 μg/kg/minute to about 5 μg/kg/minute, more preferably in the range of 0.2 μg/kg/minute to about 4 μg/kg/minute, even more preferably in the range of 0.5 μg/kg/minute to about 3 μg/kg/minute, even more preferably in the range of 0.75 μg/kg/minute to about 2 μg/kg/minute, and most preferably about 1 μg/kg/minute. Therefore depending on the IV volume, the administration time, and the weight of the subject nitroglycerin will be added in an amount sufficient to obtain the desired range (i.e. 1 μg/kg/minute). If a transdermal system is used the delivery of nitroglycerin should preferably be between 0.2 mg/hr and 1 mg/hr, more preferably between 0.3 mg/hr and 0.8 mg/hr, and even more preferably between 0.4 mg/hr and 0.6 mg/hr. It is anticipated that the package will contain freeze dried L-arginine in a glass bottle to which the nitroglycerin and sterile water would be added in such as fashion as to have 30 grams of L-arginine and 1 to 960 milligrams of nitroglycerin all diluted to a total volume with sterile water of 300 cc. Alternatively, nitroglycerin, L-arginine, and water can be added in sterilized glass bottles and adjusted to a physiological pH. The pH on reconstitution in water should preferably be in the range of approximately 5–8, more preferably in the range of 6–7.5, even more preferably in the range of 7 to 7.5, and even more preferably approximately 7.4 which is physiologic in order to avoid the present problem that is present in those solutions that require the pH limitation of 5.6 to avoid bacteriologic overgrowth on periods of prolong standing when shipped in solution.

The dose of nitroglycerin might vary according to future studies on the effect of the combination ratio on heart rate. In addition even though the discussion focuses on intravenous administration, buccal, intracoronary, intramuscular, topical, intranasal, rectal, sublingual, oral, subcutaneous, or patch administration forms alone or in combination apply as well. Because of their compatibility, the combination of L-arginine and nitroglycerin in patch may be the most common use as is the case presently for the use of nitroglycerin alone in patch form. The feasibility of patch technology is supported by solubility test of L-arginine in Tridil™. Solubility test demonstrated the following: without the addition of water, approximately 170 mg of L-arginine will dissolve in 1.0 ml of Tridil™ (5 mg of nitroglycerin/ml); a clear colorless mixture was obtained when 2500 mg of L-arginine hydrochloride, 1.0 ml of Tridil™, and 2.8 ml of deionized water were combined at 30° C. with gentle swirling and then cooled to ambient temperature (approximately 24° C.); and a very thick, yet pourable, slurry was obtained when 2500 mg of L-arginine, 1 ml of Tridil™, and only 0.5 ml of deionized water were combined. These results suggest that L-arginine and Tridil™ have a great degree of solubility compatibility and therefore could easily be incorporated into the current patch administration technology.

The following illustrate the above described mechanism of action and treatment of cardiocerebropulmonorenovascular diseases:

EXAMPLE 1

It was recently discovered that dogs treated to a floor of nitroglycerin effect could be made further responsive by the co-administration of nitroglycerin and L-arginine in water in a manner similar to that commonly seen clinically with the addition of sodium nitroprusside (SNP) to nitroglycerin; however, when compared to SNP, L-arginine combined with nitroglycerin had much more favorable hemodynamic effects. Compared to SNP, vascular resistance was reduced by 50%, cardiac output doubled, and contractility increased. This led to the hypothesis that the combination of L-arginine and nitroglycerine was generating EDRF as opposed to SNP which is known to produce nitric oxide in a direct fashion.

Since there is still debate whether EDRF is identical to nitric oxide it was hypothesized that EDRF not being identical to NO would account for the difference in hemodynamic effect. To account for the extra EDRF it was hypothesized that nitroglycerin in addition to being a pro-drug for nitric oxide was also an agonist to cNOS activation and that L-arginine rate limitations in the canine model could be explained by a supply-demand mismatch in L-arginine uptake particularly in disease state such as hypertension, hyperlipidemia, arteriosclerosis involving the endothelial cell which is thought to be an active transport process with potential rate limitations which can possibly be overridden by passive diffusion of L-arginine given in excess. Hence, the rational for combining L-arginine with nitroglycerin for the treatment of nitrate resistance and tolerance. To test this hypothesis, the effects of exposing intact rat aorta to nitroglycerin combined with L-arginine in aqueous solution was studied and the results were compared to the results obtained with SNP combined in an aqueous solution with L-arginine. The effect of combining L-arginine and nitroglycerin appear in FIG. 2. The clinical preparations were as follows:

ANIMAL PREPARATION

Eight Sprague-Dawley rats were used in this nitroglycerin study and two were used in the SNP study. Following removal of the aorta from each rat the aorta was cleaned and cut into 5 segments. The segments were randomly distributed to minimize variation in baseline values. Following this, the segments were incubated in Earl's Salt solution at 37° C.

TREATMENT PROTOCOL

Nitroglycerin Group—one of the five segments removed served as control to assess the integrity of the endothelium (basal activity). The other four each received 50 µmol of L-arginine. After 30 minutes 1 ml of IBMAX (50 µmol) was added to the 5 segments to prevent any further cGMP degradation by phosphodiesterase (IBMAX is isobutyl methyl xanthine). The 5 segments were treated as follows: A—control-basal activity; B is L-arginine group—50 µmol L-arginine added to basal group; C is the nitroglycerin group—5 µmol nitroglycerin in L-arginine 50 µmol; D is nitroglycerin+$N^G$-nitro-L-arginine methyl ester (L-NAME a known inhibitor of NOS function) group—5 µmol nitroglycerin+0.5 m mol of L-NAME and L-arginine 50 µmol; and E is the L-NAME group—0.5 m mol of L-NAME and L-arginine at 50 µmol. After 50 minutes each of the segments were removed and placed in 500 µL of 0.1 NHCl. They were left for one hour at which time they were removed and weighed.

CYCLIC GMP ASSAY

For cGMP determination 400 µL of HCl solution remaining after strips were removed and weighed were transferred into gama flow tubes and cyclic GMP was determined by radioimmunoassay.

DATA INTERPRETATION

A. Control—Basal. This represents cGMP activity at baseline that was generated by resting NO sources of soluble guanylate cyclase activation, i.e. baseline.

B. L-arginine Group. This represents cGMP activity generated by L-arginine and EDRF (endogenous or "native" NO production).

C. Nitroglycerin Group. (L-arginine plus nitroglycerin) The cGMP activity represents the sum of B (L-arginine) plus nitroglycerin induction of cNOS and the subsequent EDRF produced in addition to nitric oxide from nitroglycerin by the L-arginine independent pathway (pro-drug effects).

D. L-NAME Group. L-arginine (L-arginine plus nitroglycerin plus L-NAME). Represents cGMP activity from nitroglycerin enzymatic conversion alone since L-NAME used in excess inhibits NOS derived EDRF from all sources.

E. L-arginine+L-NAME—represents cGMP activity due to non-nitric oxide sources activating soluble guanylate cyclase activation and was subtracted from all measurements to eliminate effects of non NO activation of cGMP. (atrial natriuretic factor, etc.)

From this it is apparent that: Total NO from nitroglycerin is C–B; NO from enzymatic degradation of nitroglycerin to NO equals D–E; EDRF (NOS) stimulation from nitroglycerin=(C–B)–(D–E)

SNP GROUP

A second group of two rats was examined, as above, only in this group SNP was substituted in the treatment protocol for nitroglycerin. These results are shown in FIG. 3. A', B', and E' correspond exactly with A, B, and E of FIG. 2. C' is equal to L-arginine at 50 µmol plus 1 µmol SNP and represents cGMP activity from L-arginine stimulation of EDRF production plus any cNOS activation by SNP plus NO from SNP by non-enzymatic conversion. It does not appear that SNP requires any sulfhydryl group, but rather that it forms NO and cyanide as a by-product nonenzymatically. D' is SNP+L-NAME—represent cGMP activity generated by non enzymatic conversion of SNP to NO alone, i.e. exogenous or "non-native" NO. Total NO from SNP=C'–B'; Total NO from SNP from non-enzymatic conversion=D'–E'; EDRF from SNP by NOS activation=(C'–B')–(D'–E').

RESULTS

FIGS. 2 and 3 summarizes these results with a bar graph representative of the respective detected picomols of cGMP/100 mg wet tissue. Although not shown in FIG. 2, when nitroglycerin and L-NAME were combined in the absence of L-arginine, similar results were obtained regarding cGMP production. In both FIGS. 2 and 3 the bar labelled NOS is the amount of "native" NO produced which is total NO minus the NO produced via the L-arginine independent pathway.

Nitroglycerin resistance—tolerance has frustrated cardiologists and pharmacologists since 1888. (Stewart D. D., 1888. *Remarkable Tolerance to Nitroglycerin.* Philadelphia Polyclinic. 172–5.) These results support the hypothesis outlined in FIG. 1B and clarify the mechanism of nitroglycerin tolerance. It is believed that an additional nitroglycerin activation site is cNOS in the endothelial cell. Under conditions leading to tolerance the agonist effect of nitroglycerin on cNOS induction leads to a depletion of L-arginine in the endothelial cell secondary to rate limitations in active L-arginine transport pump kinetics in FIG. 1A and FIG. 1B. This creates a supply demand mismatch situation at the membrane uptake step and explains why arginine is rate limiting in a canine model. This may also explain why during administration of nitroglycerin a nitrate free interval is required. It is believed that this is necessary so that the endothelial cells can replete the deficient L-arginine by active transport. By adding L-arginine with or without self-hydrial reducing agent compounds to nitroglycerin it is believed that EDRF can be generated, and in the process a significant reduction in clinical and mortality endpoints can be obtained relative to using nitroglycerin alone or in combination with SNP or other donors of exogenous NO.

The fact that veins are more sensitive to exogenous NO (and most likely "native" NO also), compared to arteries, explains why at low doses nitroglycerin is principally a venous dilator compared to SNP which is a balanced arterial venous dilator. It explains why at 37 micrograms/hr nitroglycerin becomes arterial because at this level all the EDRF potential is realized and pro-drug conversion of NO takes over as the last source of nitric oxide generated by nitroglycerin. This last source of NO generated from pro-drug conversion is equivalent to NO from SNP and generates a similar arterial effect.

It is possible that EDRF is not identical to NO and is possibly the precursor (L—OH—NO half life of 3–50 seconds) for NO. This would seem to explain failed attempts to substitute SNP for nitroglycerin in clinical situations, such as unstable angina and acute myocardial infarction (Flaherty, J. T., M.D., 1983, *Comparison of Intravenous Nitroglycerin and Sodium Nitroprusside in Acute Myocardial Infarction*. American Journal of Medicine. 53–60.) since EDRF has better anti-ischemic actions and since EDRF would not be produced using SNP, SNP would not lead to the benefits in mortality potentially realizable with nitroglycerin. Another beneficial effect of EDRF produced by cNOS stimulation with nitroglycerin may result from the ability of EDRF to function as a free radical scavenger relative to exogenous NO. (Zembowicz A., et al., 1991, *Nitric Oxide and Another Potent Vasodilator are Formed from $N^G$-hyroxy-L-arginine by Culture Endothelial Cells*. Pharmacology. Proc. Natl. Acad. Sci. USA 88:11172–76.) In a reperfusion injury a free radical scavenger (possibly EDRF) is needed to absorb the free radicals which appear to be what is happening with L-arginine and nitroglycerin but not with SNP, a non-native source of NO. This can be explained because one would not expect to see the intermediate EDRF with SNP. Tolerance is established and the beneficial effect of nitroglycerin is lost because there is no longer any EDRF being produced or at least until the rate limiting step is overcome by adding L-arginine substrate. However, it has been shown that if there is insufficient L-arginine in the cells containing phelos molecular $O_2$ functions as an alternative substrate with $O_2^-$ and $H_2O_2$ resulting. Therefore, adding L-arginine with or without a sulfhydryl reducing agent would limit the formation of free radical production. This serves an additional mechanism of benefit from the combination with or without self-hydrial reducing agents because it relates to the fact that used alone nitroglycerin soon loses its beneficial effect in limiting reperfusion injury with patients who have had recent heart attacks and abrupt restoration of blood flow. The same thing is seen in patients who are undergoing re-establishment of blood flow after coronary bypass operations coming off the bypass pump. This form of reperfusion injury is thought to be mediated by free radical generation of reperfusion and preliminary data especially in cats show that L-arginine administered alone also limits free radical production. Therefore, the combination would be likely to limit reperfusion injury relative to nitroglycerin used alone.

These results indicate the formation of a new drug by combining nitroglycerin with L-arginine in excess so as to take advantage of passive diffusion override mechanism of the endothelial cells membrane transport pump as a treatment for nitroglycerin resistance-tolerance. Such a formulation has applications which include hypertension, hypertensive heart disease, coronary heart disease (angina, myocardial infarction, sudden death), cardiovascular diseases (congestive heart failure, stroke, peripheral vascular disease), cerebrovascular ischemia (TIA), and renovascular ischemia, and pulmonary hypertension.

Another potential utility of this complex is to independently produce EDRF as seen here in rat aorta and the canine results which will be of great value as a treatment for tolerance of nitroglycerin without additional toxicity or inconvenience in administration of nitroglycerin presently used alone. The method of administration would be unchanged.

An eight hour infusion in a normal human volunteer has been performed using a wide range of nitroglycerin concentrations ranging from 12.5 mg /250 cc total volume through 100 mg/250 cc total volume 10% L-arginine and found most importantly the absence of tachycardia previously reported with either L-arginine or nitroglycerin alone. In addition with 2½ times the currently approved dosages of L-arginine exposure (75 g total) there was no evidence of metabolic acidosis from the HCL present in the L-arginine formulation currently approved. This study is summarized below.

EXAMPLE 2

The following study is a normal human volunteer dose ranging study for intravenous nitroglycerin combined with L-arginine. The objective of this study was to examine the combined administration of intravenous nitroglycerin with L-arginine 10% (aqueous) for the following:

1. Reflex tachycardia (baroreceptor reflex activation).
2. Hypotensive activity (therapeutic effect).
3. Metabolic disturbances-metabolic acidosis.
4. Electrocardiographic abnormalities with prolonged infusion.

The patient studied in this dose ranging study was a 47 year old normotensive white male with no prior history of illness or hospitalization and on no chronic medications.

The materials utilized in this study consisted of the following:

1. Tridil brand of intravenous nitroglycerin (5 mg per cc).
2. 10% L-arginine in water (R-Gene™-KABI).
3. Normal saline.
4. 5×150 cc vacuum sealed sterile bottles.
5. Two Ivac Pumps to include a 3 way stopcock for alternating infusions of drug and saline.
6. One Propac cardiac monitor.
7. One Spacelabs 2000 24 hour blood pressure monitor.
8. One Cardionostics Dural-Lite model #2011 holter recorder.

Patient preparation consisted of pretreatment with 40 mg of Pepcid (famotidine-MERCK) and 50 mg of benadryl the night before. 50 mg of benadryl was repeated on the morning of the study. This was done for the purpose of blocking $H_1$ and $H_2$ receptors from any possible activation by L-arginine.

On the morning of the study a baseline EKG was obtained along with Serum Chemistries and Complete Blood Count (CBC). Following this the 24 hour holter monitor, ambulatory blood pressure monitor, and Propac were attached. The blood pressure monitor was calibrated against the Propac and a discrepancy of approximately 20 mmHg of systolic and 10 mmHg of diastolic blood pressure was observed in the left verses right arms respectively. Next, an IV was established in the left foot in the left saphenous vein with an 18 gauge angiocath. An initial maintenance infusion with saline was begun at KVO (keep vein open) rate. Following this six rapid dose response titrations were performed over the following 8 hours and are shown in FIG. 4 with ¼ (bottle #1), ½ (bottle #2), and full strength nitroglycerin in 10% L-arginine (bottle #3). This was followed by a full strength nitroglycerin infusion in water without L-arginine (bottle #4). Next an infusion of pure L-arginine 10% was administered without nitroglycerin in 10% L-arginine (bottle #5). Lastly an infusion consisting of double strength nitroglycerin in 10% L-arginine (bottle #6) was administered. Full strength nitroglycerin was defined as 50 mg of nitroglycerin in a total volume of 250 cc of L-arginine 10% in water or water alone (bottle #4).

With each infusion, the initial rate was 25 cc per hour. Following this the infusion was doubled to 50 cc per hour. This was increased by 50 cc per hour every 5 to 10 minutes until a total infusion rate of 300 cc per hour was achieved. During these infusions blood pressure and heart rate data were recorded every 2 minutes by Propac before increasing the rate of infusion as described above. During bottle changes the infusion was changed to normal saline at 100 cc per hour. At the beginning of each infusion an estimated 10 cc of "dead space" was eliminated from the infusate left over from the previous bottle by running the first 10 cc at a "wide open" rate. Then the 25 cc sequence was re-initiated as previously described above.

Following the final infusion a repeat of Serum Chemistries, CBC, and EKG were obtained.

For each infusion systolic and diastolic right arm blood pressures were averaged. Heart rate was likewise averaged. These averages were obtained by taking each individual reading obtained every two minutes, totaling them, and dividing the period in which the infusion occurred (measurements in between infusions during bottle changes not included).

The results are summarized in FIG. 4. In FIG. 4 SBP means Systolic Blood Pressure, DBP means Diastolic Blood Pressure and HR means Heart Rate. There does not appear to be any evidence of reflex tachycardia with the ratio of nitroglycerin to L-arginine used in FIG. 4. There was a dose dependent blood pressure reduction along with a trend toward dependency on nitroglycerin concentration.

There was no evidence of metabolic acidosis developing secondary to L-arginine infused for a prolonged period to the total dose of 75 grams administered over 8 hours. There was no evidence of arrhythmia. There was no evidence of electrocardiographic abnormalities. Clearly, this indicates that the administration of the combined L-arginine/nitroglycerin does not have the adverse consequences seen with either L-arginine or nitroglycerin when administered alone.

The foregoing description of the invention is illustrative of the preferred embodiments of the invention currently contemplated by the inventor thereof. However, it should be clear that the foregoing description of the invention is not to be interpreted in a limitative manner, there being several equivalent systems and manners of performing the present invention. For example, the L-arginine is contemplated to be derived from commercially available products such as R-Gene™ or any other source of pharmaceutical grade L-arginine, and the nitroglycerin can be obtained from a variety of delivery systems well known in the art for nitroglycerine alone, for example: lingual aerosols such as Nitrolingual™ spray (0.4 mg/metered dose from Poulenc Rorer); transdermal systems such as Minitran™ (.6 mg/hour from 3M); topical ointments such as Nitro-Bid™ Ointment (2% from Marion Merrell Dow as well as tablet and patch form (currently using commercial patch product called Tridil™ from Du Pont). This list is not all inclusive, but is merely meant as a representation of the variety of nitroglycerin delivery systems which could be easily modified to be a delivery system for the combination of L-arginine and nitroglycerin. All that is required is compatible systems for the simultaneous delivery of nitroglycerine and L-arginine. Such a selection of delivery systems and commercial starting materials does not depart from the scope and spirit of the present invention.

STABILIZER DATA

L-Arginine-hydrochloride is an effective Stabilizer for Nitroglycerine to determine whether L-Arginine is a suitable stabilizer of nitroglycerine to enable safe handling of a mixture of the two. Nitroglycerine was mixed with L-Arginine and the mixture was manipulated with a spatula.

The method of Richman, Fox and Shangraw (*Journal of Pharmaceutical Sciences*, 1965, 54, 447) was used with modifications to isolate the nitroglycerine. A sample of 50 nitrostat sublingual tablets (0.4 mg nitroglycerine/tablet to total 20 mg of nitroglycerine) was placed in 125 mL Erlenmeyer flask equipped with a magnetic stirrer. Approximately 50 mL of acetone was added to the flask, the flask was covered with a watch glass, and stirring was commenced to break up the tablets and dissolve the nitroglycerine. The resultant slurry was filtered through a fritted funnel to remove the lactose and a nine-fold excess (184 mg) of L-Arginine-hydrochloride was added to the solution. Evaporation of the acetone afforded a white, semi-translucent solid which could be broken apart with a metal spatula and handled without noticeable changes. The results obtained indicate that nitroglycerine is stabilized in a matrix of L-Arginine hydrochloride and can be handled.

DATA FOR COMPATIBILITY WITH N-ACETYL CYSTEINE

An Orion Research model 501 pH meter was calibrated using pH 7.00 and pH 4.00 buffer solutions. To a 50 mL capacity screwtop vial was added 1.502 g of L-arginine hydrochloride (Tanabe) and 15 mL of deionized water. Swirling for approximately 30 seconds effected dissolution resulting in a clear, colorless solution of pH of 7.02. After standing for two days, 1.504 g of N-acetylcysteine was added and required four to five minutes of vigorous swirling an shaking to dissolve. The resulting clear colorless solution was determined to have a pH of 2.38. The appearance and pH were unchanged upon addition of 0.6 mL of tridil (5 mg/mL).

From these results L-arginine, nitroglycerin and N-acetylcysteine are compatible in aqueous solution. It is probably desirable to titrate the solution to a higher pH using an appropriate method such as addition of external base, utilizing a greater portion of the free base of L-arginine, or use of the conjugate base of N-acetylcysteine in a proper ratio with existing species present.

The true scope of the invention is only to be defined by the claims appended hereto.

What is claimed is:

1. A formulation comprising a biological equivalent of arginine and an agonist of nitric oxide synthase, said agonist being different than said biological equivalent of arginine.

2. The formulation of claim 1, wherein said agonist is nitroglycerin.

3. The formulation of claim 1, wherein the biological equivalent of arginine is citrulline.

4. The formulation of claim 1, wherein the biological equivalent of arginine is an arginase inhibitor.

5. The formulation of claim 1, wherein the biological equivalent of arginine is an antioxidant.

6. The formulation of claim 1, wherein said biological equivalent of arginine is hydralazine.

7. The formulation of claim 1, wherein said biological equivalent of arginine is lysine.

8. The formulation of claim 4, wherein said arginase inhibitor is comprised of ornithine.

9. A method of treating a disease condition in a subject by vasodilation or vasorelaxation comprising:
   selecting a subject;
   mixing a biological equivalent of arginine and an agonist of nitric oxide synthase, said biological equivalent of arginine being different from said nitric oxide synthase;
   administering to said subject a formulation comprising said mixture;
   obtaining periodic indicators of vasorelaxation for the subject; and;

continuing administration of the formulation until a desirable state of vasorelaxtion is obtained.

10. The method of claim 9, wherein said biological equivalent of arginine is citrulline.

11. The method of claim 9, wherein said biological equivalent of arginine is selected from the group consisting of hydralazine, Vitamin E, minoxidil, procardia, papaverine, nycetapine, and calcium antagonist.

12. The method of claim 9, wherein said agonist of nitric oxide synthase is a nitrate.

13. The method of claim 12, wherein said nitrate is nitroglycerin.

14. The method of claim 9, wherein said biological equivalent of arginine is comprised of an arginase inhibitor.

15. The method of claim 9, wherein said biological equivalent of arginine is lysine.

16. The method of claim 9, wherein said biological equivalent of arginine is ornithine.

17. A method of treating nitrate tolerance in a mammal, comprising:

administering a biological equivalent of arginine to said mammal when nitrate tolerance is indicated in said mammal;

continuing administration of said biological equivalent of arginine until tolerance is ameliorated.

18. The method of claim 17, wherein said nitrate is nitroglycerin.

19. The method of claim 18, wherein said biological equivalent of arginine is administered in excess of said nitrate.

20. The method of claim 17, wherein the biological equivalent of arginine is an arginase inhibitor.

* * * * *